(12) United States Patent
Studer

(10) Patent No.: US 9,931,102 B1
(45) Date of Patent: Apr. 3, 2018

(54) SPECIMEN COLLECTION SYSTEM FOR USE WITH URINAL

(71) Applicant: Kimberly A. Studer, Austin, TX (US)

(72) Inventor: Kimberly A. Studer, Austin, TX (US)

(*) Notice: Subject to any disclaimer, the term of this patent is extended or adjusted under 35 U.S.C. 154(b) by 236 days.

(21) Appl. No.: 14/326,238

(22) Filed: Jul. 8, 2014

(51) Int. Cl.
*A61B 5/00* (2006.01)
*A61B 10/00* (2006.01)
*A61G 9/00* (2006.01)

(52) U.S. Cl.
CPC ............ *A61B 10/007* (2013.01); *A61G 9/006* (2013.01)

(58) Field of Classification Search
CPC .. A61B 10/007; A61B 10/0045; A61B 5/1405
USPC ....................................................... 600/573
See application file for complete search history.

(56) References Cited

U.S. PATENT DOCUMENTS

| | | | |
|---|---|---|---|
| 3,161,891 A | 12/1964 | Bauman | |
| 3,485,233 A | 12/1969 | Cord | |
| 1,026,433 A | 5/1977 | Crippa | |
| 4,106,490 A | 8/1978 | Spilman et al. | |
| 4,276,889 A | 7/1981 | Kuntz et al. | |
| 4,393,881 A * | 7/1983 | Shah .................... | A61B 10/007 600/573 |
| 4,492,258 A | 1/1985 | Lichtenstein et al. | |
| 4,895,167 A | 1/1990 | Guala | |
| 5,797,855 A | 8/1998 | Hazard et al. | |
| 5,842,233 A | 12/1998 | Broden | |
| 5,926,858 A | 7/1999 | Heller | |
| 6,070,275 A | 6/2000 | Garlock | |
| 6,098,210 A | 8/2000 | Broden | |
| 6,409,971 B1 * | 6/2002 | Wilkinson ......... | A61B 10/0045 422/537 |
| 6,684,414 B1 | 2/2004 | Rehrig | |
| 6,968,577 B1 | 11/2005 | Taft, Jr. | |
| 7,871,385 B2 | 1/2011 | Levinson | |
| 8,597,207 B1 | 12/2013 | Perry | |
| 2003/0053938 A1 * | 3/2003 | Szeles .................. | A61B 10/007 422/400 |
| 2003/0164051 A1 * | 9/2003 | Kunimune ........... | A61B 10/007 73/863.23 |
| 2007/0025886 A1 * | 2/2007 | Yong .................. | A61B 10/0045 422/400 |

* cited by examiner

*Primary Examiner* — Daniel Cerioni
(74) *Attorney, Agent, or Firm* — Scheinberg & Associates, P.C.; John B. Kelly

(57) ABSTRACT

A urine collection method and apparatus, the apparatus including a storage container for holding urine; a first closeable opening in the storage container for allowing urine to enter and exit the storage container, the shape of the opening configured for contacting a patient to allow the patient to urinate into the storage container; a second opening for allowing fluid transfer from the interior of the storage container to the exterior of the storage container; vacuum a seal for the second opening, the seal maintaining the urine within the storage container being sealed until an analysis vial is connected to the urine collection apparatus, the connection of the analysis vial opening the seal to allow urine to leave the storage container when the analysis vial is connected.

6 Claims, 7 Drawing Sheets

SPECIMEN COLLECTION SYSTEM FOR USE WITH URINAL

TECHNICAL FIELD OF THE INVENTION

The present invention relates to a method and apparatus for collecting and transferring urine safely and efficiently for sample analysis.

BACKGROUND OF THE INVENTION

Urinalysis is a common method used by medical professionals to diagnose a patient. It is a laboratory test performed to determine problems with a patient with factors that can appear in urine. These factors can be characteristic of many illnesses and disorders that affect how the human body removes waste and toxins. Problems with any of the lungs, kidneys, urinary tract, skin, and bladder can affect the appearance, concentration, and content of urine.

In order to obtain urine from a patient, the patient is often required to urinate into a container. These containers are typically known as urine collection devices (UCDs). After obtaining samples in these containers, medical professionals often are required to transfer the urine from the containers into vials or storage tubes for analysis, often through an intermediary transfer cup. This process is inefficient, poses a threat to contaminating the sample, and increases the risk of body fluid exposure to persons handling the sample. The terms "vials" and "storage tubes" are used, herein, interchangeably.

Spilling urine during transfer of the collected sample to the transfer cup is a common occurrence. Directly pouring the urine into the transfer cup from the urine collection device can cause the cup to overflow or the urine to spill on the vial and/or container itself as well as any other surfaces nearby. This process can cause contamination of these surfaces, such as a laboratory table, and negatively affect the accuracy of the urinalysis and other tests performed on the same surfaces. Spilling urine can also cause the urine and another other infectious agents in the urine get on the medical professional's clothing, or other safety equipment, requiring them to change out of the contaminated articles. Labels on the outside of the UCDs as well as the transfer cups can become illegible when urine comes into contact with the ink on the label. These occurrences require additional time and effort to remedy as well as excess use of supplies.

Some attempts at resolving the above issues have been made. U.S. Pat. No. 4,026,433 (Crippa) describes a testpiece that is tightly coupled to a downwardly extending tubular member of a glass receptacle with a cover. The urine is collected by the glass receptacle and then the cover is fitted over it. The testpiece is physically attached to the glass receptacle over the outside of the tubular member, and then liquid is transferred to the testpiece by tilting the receptacle to allow the urine to flow over the edge of the tubular member into the testpiece. However, if any urine seeps into the interface area where the tubular member and testpiece facilitate attachment, the tight coupling of the two pieces will become undone and the testpiece could fall off.

U.S. Pat. No. 4,492,258 (Lichtenstein) discloses a collection apparatus with a collection chamber for a sample of urine. Once the collection chamber is filled with fluid, the excess urine is collected in a container surrounding the chamber. A drain passage is connected to the excess urine container for runoff urine to flow once the container is filled. The urine in the collection chamber, however, still needs to be transferred into an analysis vial for testing.

U.S. Pat. No. 7,871,385 (Levinson) describes another collection apparatus with a collection chamber for a sample of urine. Once, the collection chamber is full, a ball within the chamber will close off the opening to the chamber and thus prevent any further urine to enter the chamber. This extra urine is then passed through an opening at the end of the apparatus into either another container or disposal. Transfer of the urine in the collection chamber to an analysis vial for testing still presents a problem.

One prior art process of transferring urine from a UCD to an analysis vial is illustrated in FIGS. 1A to 3. FIG. 1A shows an analysis vial 101. The interior of the tube is maintained at a vacuum and is sealed by stopper 102. An optional volumetric grid (not shown) and label 115 may be seen on the outer surface of the analysis vial 101.

FIG. 1B shows a transfer cup 103. The transfer cup has a body portion 104 typically made of plastic, though other materials can be used such as glass. The transfer cup also consists of a screw cap 105, containing an integrated transfer apparatus 106, for closing the cup. A label 107 covers the opening to the integrated transfer apparatus 106 in the screw cap 105 and can be peeled back to expose a needle 108 in the center of the opening. The needle is contained in a rubber sheath (not shown), which if pushed towards the lid exposes the needle for fluid transfer. For example, when the analysis vial is pushed against the transfer cup to insert the needle of the transfer cup in the analysis vial, the rubber stopper is pushed back and exposes the needle. FIG. 1C shows a transfer straw 109 that can be used with transfer cup 103 instead of the integrated transfer apparatus 106 in screw cap 105. The transfer straw 109 is a non-sterile, plastic holder device that contains a needle 111 that is held in place by a portion 110 of the plastic holder device. Needle 111 is surrounded by a rubber sheath 115, which can be retracted by pushing an analysis vial towards the needle 111. FIG. 1D shows another type of urine collection device, a urinal 112, which can be used for urination by bedridden patients. It is sometimes necessary to collect a sample from the urinal of a bedridden patient. The body of the urinal is ribbed for strength and has an optional measurement grid (not shown) to determine the volume of the fluid inside. The urinal 112 has an opening 113 for urine to enter when in use and has an optional lid (not shown) over opening 113 to prevent spilling and reduce odor. The opening 113 is angled from the main body of the urinal for ease of use. A handle 114 also extends from the main body of the urinal for convenience purposes. FIG. 1E shows a female adapter 115 for the urinal 112.

FIG. 2 shows a prior art method of collection of urine and transferring a sample to an analysis vial using the devices illustrated in FIGS. 1A to 1D and is illustrated in FIG. 3. In Step 200, urine is collected in urinal 112. Arrow 116 represents the flow of urine into the urinal, in which the urine 115 collects at the bottom of the container. In Step 202, urine 115 is transferred from the urinal 112 to the body portion 104 of the transfer cup 103. In Step 204, urine 115 is transferred to the analysis vial 101 from the transfer cup 103. This can be performed either with the integrated transfer apparatus 106 in the screw cap 105 of the transfer cup 103 or using a transfer straw 109 placed in the urine 115 in the body portion 104 of the transfer cup 103. The analysis vial 101 is pushed stopper 102 side down into either the opening in the screw cap 105 or into the opening in the top of the transfer straw 109. The needle 111 located in the integrated transfer apparatus 106 and the transfer straw 109 punctures the stopper 102 and urine 115 enters the interior of the analysis vial 101 from the needle 111. Once an adequate amount of urine 115 enters the analysis vial 101, the analysis vial is pulled from away from the transfer cup 103, sealed, labeled, and stored.

In some methods of urine collection, the transfer cup 103 acts as the urine collection device, and the urinal 112 is not used. However, this method results in splashing and spilling of the urine while the patient urinates into the cup more frequently.

This method presents several contamination and safety threats. The urine could be spilled from transfer from the urinal to the transfer cup. Using multiple devices increases the potential that one of those devices has been exposed to a contaminant and would thus introduce a contaminant to the urine in any of the devices. Since a needle is present within the integrated transfer apparatus in the screw cap of the transfer cup and within the transfer straw, safety concerns are raised with regards to accidentally puncturing the gloves or skin of medical professionals handling the transfer of urine to the analysis vials. A more streamlined and efficient apparatus is needed for the transfer of urine from a urine collection device to an analysis vial.

SUMMARY OF THE INVENTION

It is an object of the invention, therefore, to provide a urine collection device with safe and efficient features to transfer collected urine to analysis vials.

Embodiments of the invention provide an apparatus and method for collecting and transferring urine from a urinal to an analysis vial. In accordance with some embodiments, a urine collection apparatus has a storage container for holding urine; a first closeable opening in the storage container for allowing urine to enter and exit the storage container, the shape of the opening configured for contacting a patient to allow the patient to urinate into the storage container; a second opening for allowing fluid transfer from the interior of the storage container to the exterior of the storage container; and a seal for the second opening, the seal maintaining the urine within the storage container being sealed until an analysis vial is connected to the urine collection apparatus, the connection of the analysis vial opening the seal to allow urine to leave the storage container when the analysis vial is connected.

In accordance with other embodiments of the invention, a urine collection apparatus has a storage container for holding urine; an opening in the storage container for allowing urine to enter and exit the storage container, the opening adapted for use by a bedridden patient; a needle for allowing fluid transfer from the interior of the storage container to the exterior of the storage container, a first portion of the needle being inside the storage container and a second portion of the needle being exterior to the storage container; and a barrier extending from the wall of the storage container, the barrier pooling urine to be in contact with the first portion of the needle.

In accordance with preferred embodiments, a method of collecting and transferring urine using a urine collection apparatus includes collecting urine in a urine collection apparatus, the urine collection apparatus comprising a first closeable opening configured for contacting a bedridden patient to allow the patient to urinate in the urine collection apparatus, a second opening for allowing fluid transfer from the interior of the storage container to the exterior of the storage container, and a seal for sealing the second opening, the seal maintaining the urine within the apparatus; connecting an analysis vial to the urine collection apparatus, the connection of the analysis vial opening the seal to allow urine to leave the storage container when the analysis vial is connected; filling the analysis vial with a desired amount of urine; and disconnecting the analysis vial from the urine collection apparatus once the desired amount of urine has entered the analysis vial, the disconnection of the analysis vial from the urine collection apparatus closing the seal to prevent urine from leaving the urine collection apparatus.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

DETAILED DESCRIPTION OF PREFERRED EMBODIMENTS

A preferred embodiment of the invention is related to a urine collection apparatus having a storage container for holding urine. An opening in the storage container allows for urine to enter and exit the storage container. Urine may enter this opening when the patient urinates into the container; and urine may exit this opening from the storage container typically when disposing of the container or during the re-sterilization of the container. A second opening is present in the storage container for allowing fluid transfer from the interior of the storage container to the exterior of the storage container. The urine collection apparatus also has a seal for the second opening. This seal maintains the urine within the storage container being sealed until an analysis vial is connected to the urine collection apparatus. The connection between the analysis vial and the urine collection apparatus opens the seal and allows urine to leave the storage container through the second opening and into the analysis vial. Disconnecting the analysis vial from the second opening seals the second opening, preventing further fluid transfer from occurring through the second opening.

In some embodiments, a needle in the urine collection apparatus can be inserted into an analysis vial to transfer urine from the urinal to the analysis vial. The needle penetrates an elastomeric seal in the analysis vial, and the elastomeric seal reseals itself when the needle is removed. In another example, the needle may be present in the analysis vial and is inserted into an elastomeric seal in the urine collection apparatus. In another embodiment, the connection of the analysis vial opens a valve, such as a spring-loaded check valve or reed valve, after a leak-proof seal is established. The valve allows the urine to flow, and the valve automatically closing when analysis vial is removed. There term "analysis vial" as used herein encompasses any container to which the urine is transferred from the urinal. For example, another type of container, such as a transfer cup or a sterile bag could be used instead of a glass or plastic vial.

In some embodiments, multiple openings in the storage container may be present. These openings may be of various sizes, shapes, and structures to facilitate fluid transfer into different types of containers.

Figure 1A:
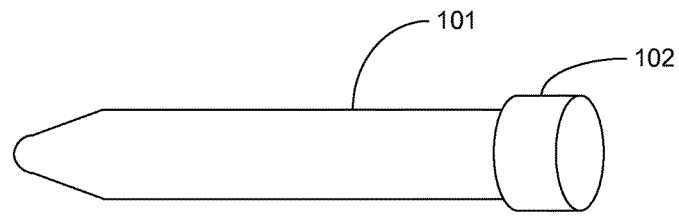
FIG. 1A shows a conventional analysis vial for urine samples.
Figure 1B:
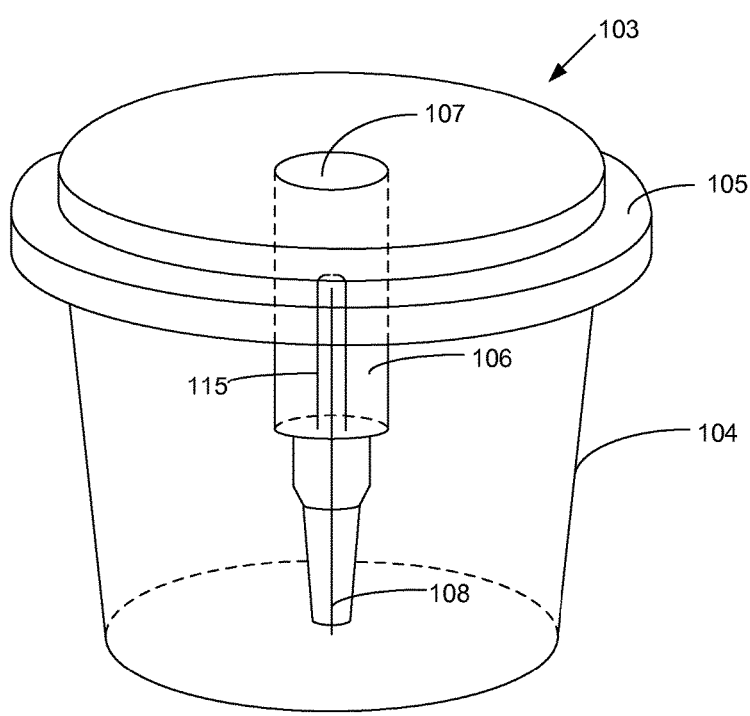
FIG. 1B shows a conventional transfer cup for urine samples.
Figure 1C:
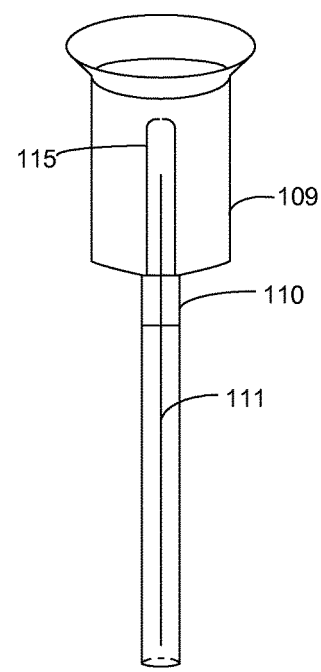
FIG. 1C shows a conventional transfer straw for use with the transfer cup of FIG. 1B.
Figure 1D:
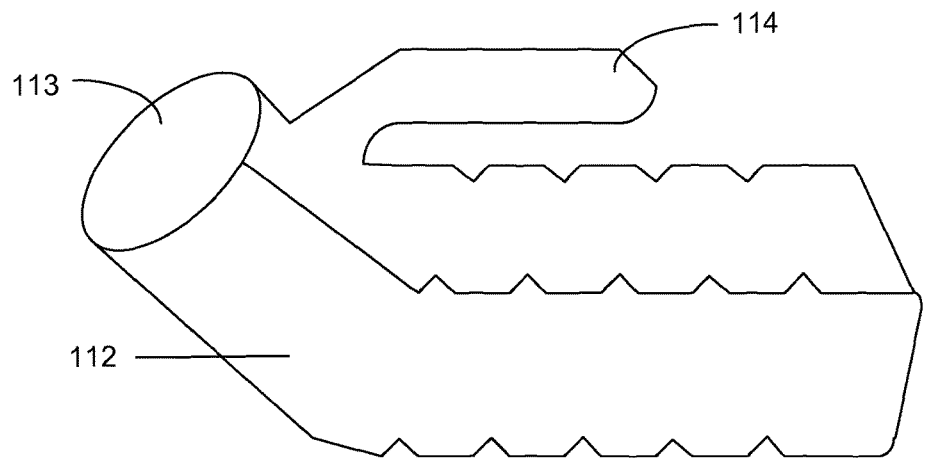
FIG. 1D shows a conventional urinal.
Figure 1E:
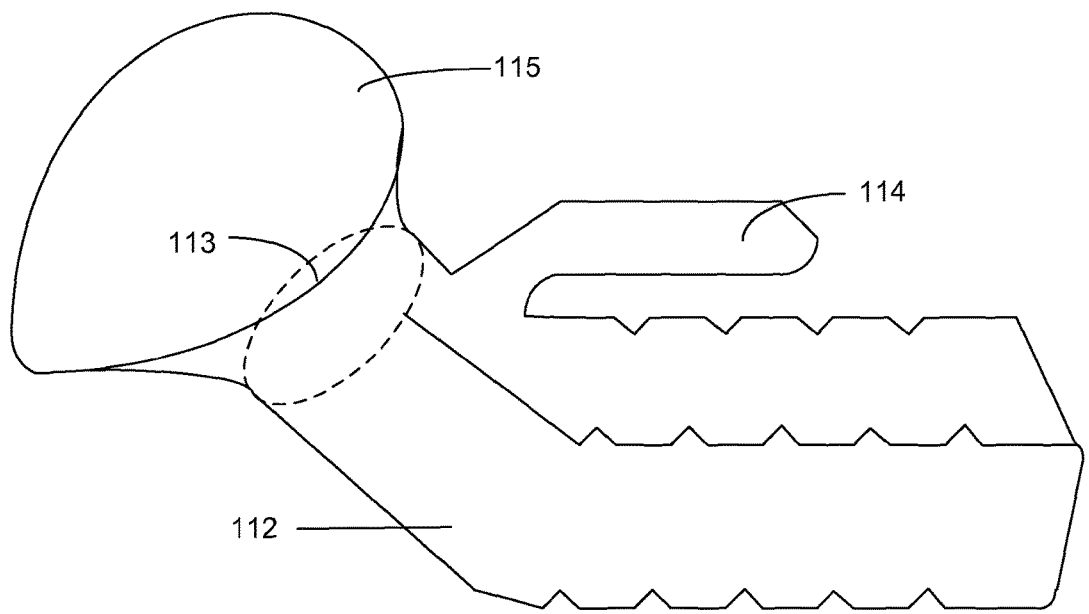
FIG. 1E shows a female adapter attached to the conventional urinal of FIG. 1D.
Figure 2:
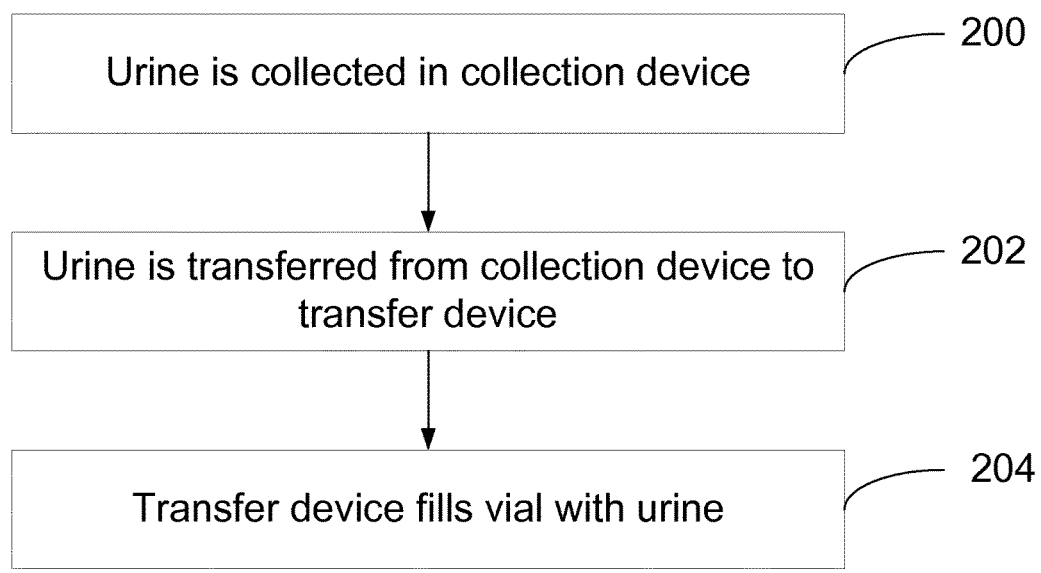
FIG. 2 describes a prior art method of transferring urine from a UCD to an analysis vial.
Figure 3:
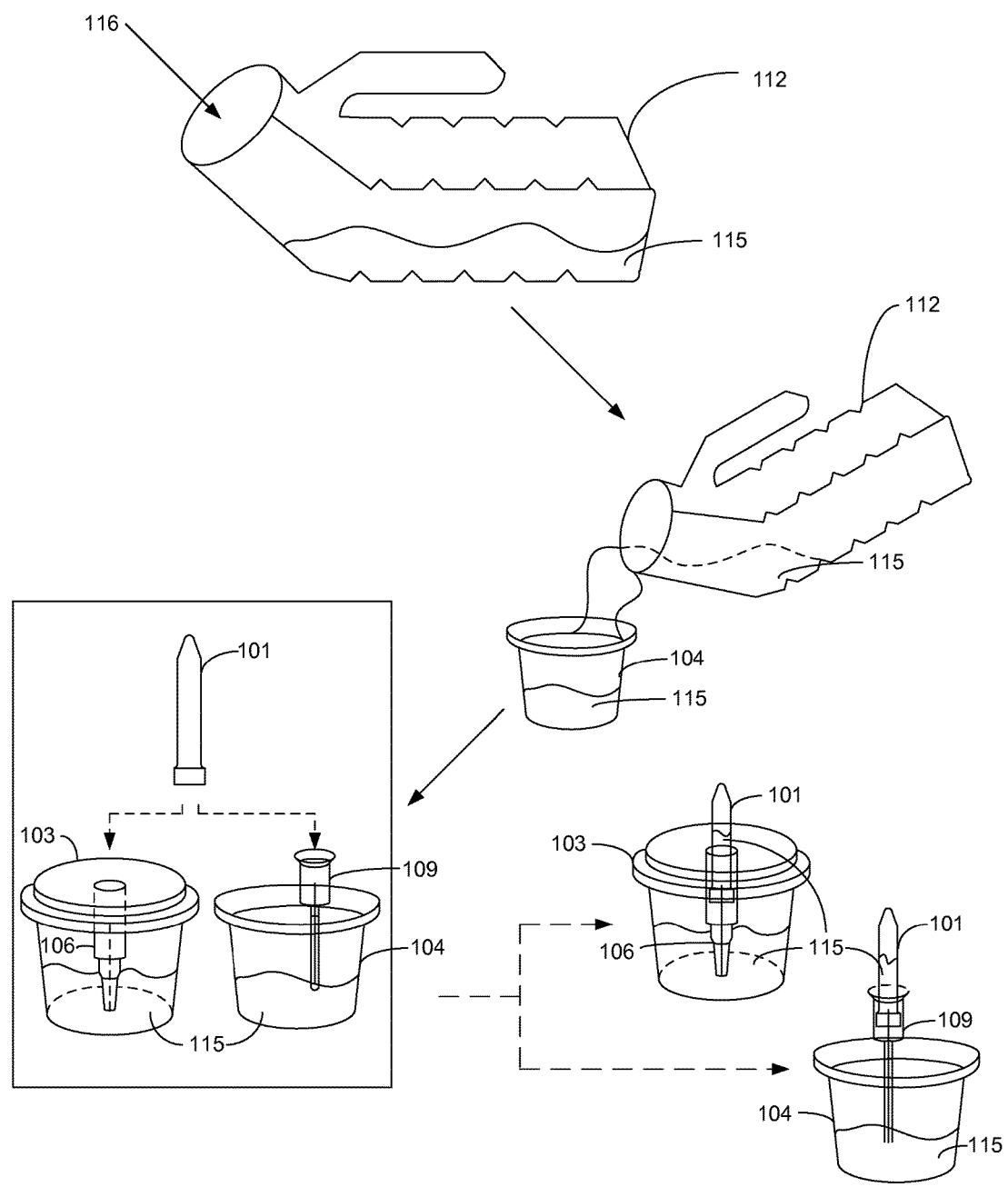
FIG. 3 illustrates the method described in FIG. 2 using the devices in FIGS. 1A to 1D.
Figure 4:
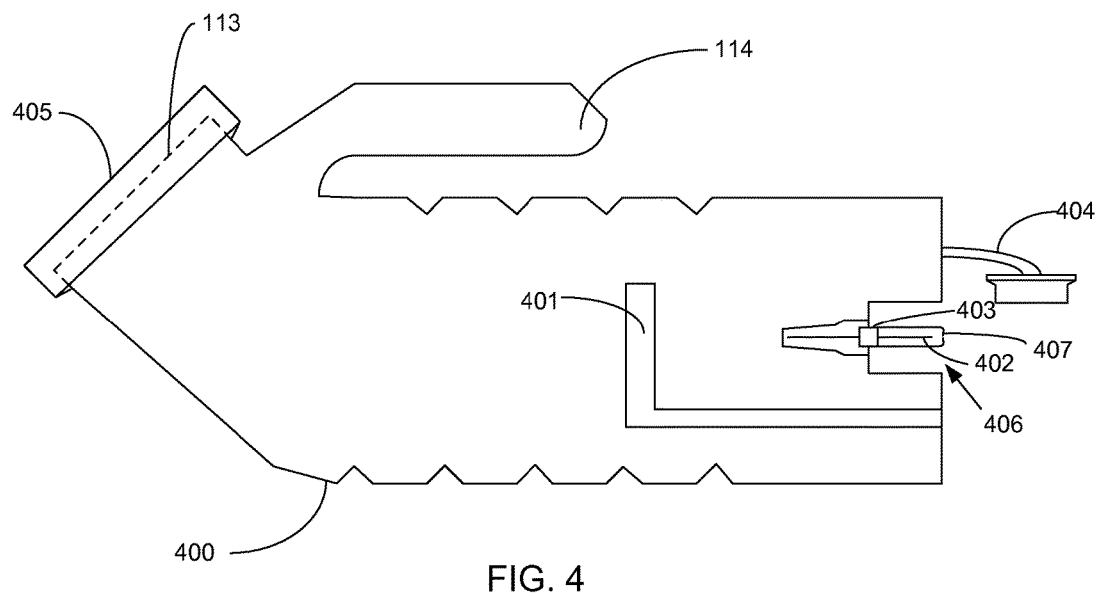
FIG. 4 shows a urinal according to an embodiment of the present invention.

FIG. 4 shows a urinal 112 according to one embodiment of the present invention. An opening 113 in the urinal 400 allows for fluids to enter and exit. The opening 113 can be closed by cover 405. The cover 405 can be screwed in over the opening 113 in the form of a screw cap or fastened on to the urinal 400 using clips. Barrier 401 extends from the wall of the urinal 400 in order to pool urine to be in contact with needle 402 in the wall of urinal 400. Barrier 401 is depicted as a two wall structure; however, barrier 401 can be any shape and size in order to facilitate pooling of the urine next to the needle 402. Needle holder 403 places needle 402 in a specific orientation with regards to the wall of the urinal 400 in which it resides. The orientation is preferably perpendicular to the wall of the urinal 400 where it is located, but any angle of the needle 402 in which a first portion of the needle 402 is internal to the urinal 400 and a second portion of the needle 402 is external to the urinal 400 can also be used. The wall 406 of the urinal in which the needle 402 is located may be indented from the surrounding wall structure in order to prevent safety hazards, such as accidental penetration of gloves or the skin, from the needle 402 being exposed past the plane of the surrounding wall structure. The needle 402 is surrounded by a rubber sheath 407, which can be retracted by pushing an analysis vial against it. A stopper 404 is attached to the exterior of the urinal 400 near the indention of the wall. The stopper 404 can be used to cover the needle 402 when not in use.

In some embodiments of the present invention, the urinal 400 is other sizes and shapes. The urinal 400 may or may not have handle 114, cover 405, and/or stopper 404. The position of the barrier and the needle in the urinal is not limited to the base of the urinal. However, the position of both features is preferably optimal for efficient transfer of urine from the urinal to the analysis vial.

Figure 5:
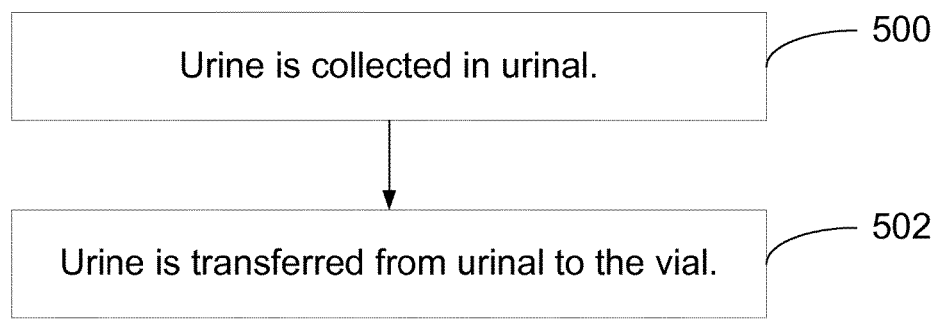
FIG. 5 describes a method of transferring urine from the urinal of FIG. 4 to an analysis vial
Figure 6A:
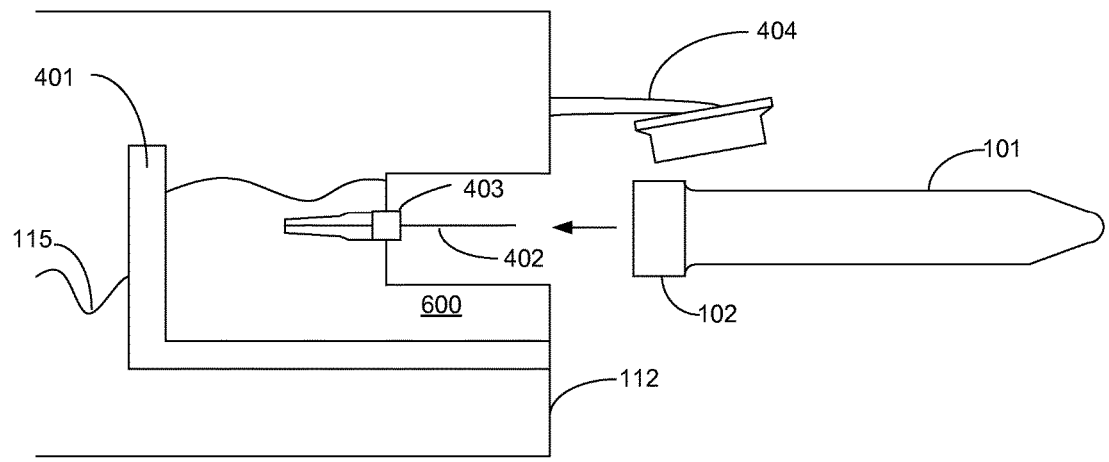
FIGS. 6A and 6B illustrate the method described in FIG. 5.
Figure 6B:
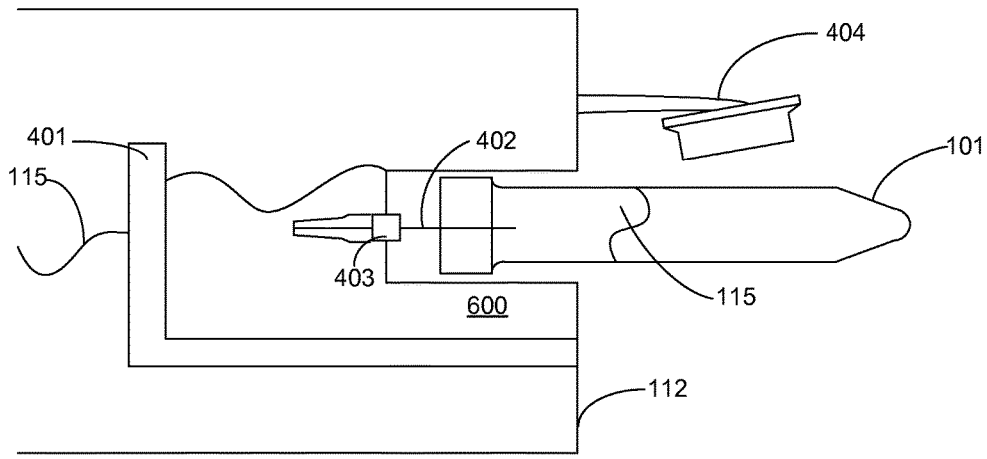

FIG. 5 shows a method, which is illustrated by FIGS. 6A and 6B, according to some embodiments of the present invention for using a urinal to transfer a sample of urine to an analysis vial. In step 500, urine is collected in the urinal from a patient. In step 502, when a sample needs to be collected from the urinal, the stopper 404 is removed from covering the needle 402. An analysis vial 101 is positioned with the stopper 102 facing the external portion of the needle 402. The urinal 400 is positioned in a way that urine 115 is pooled by barrier 401 so that the urine 600 is in contact with the needle 402. The analysis vial 101 is then pushed against the needle 402 so that the external portion of the needle 402 pierces the stopper 102 of the analysis vial 101. Because the inner environment of the analysis vial 101 is a vacuum, the urine 600 from the urinal 400 will flow to the analysis vial 101 through the needle 402. Once an adequate amount of urine 600 has entered the analysis vial 101, the vial is removed from the needle and stored for further use. The rubber sheath surrounding the needle 402 is not shown in FIGS. 6A and 6B for clarity purposes. The analysis vial can be similar to Vacutainer® specimen tube from Becton Dickinson, Franklin Lakes, N.J., and the connection mechanism can be similar to that used in the Vacutainer system.

Figure 7:
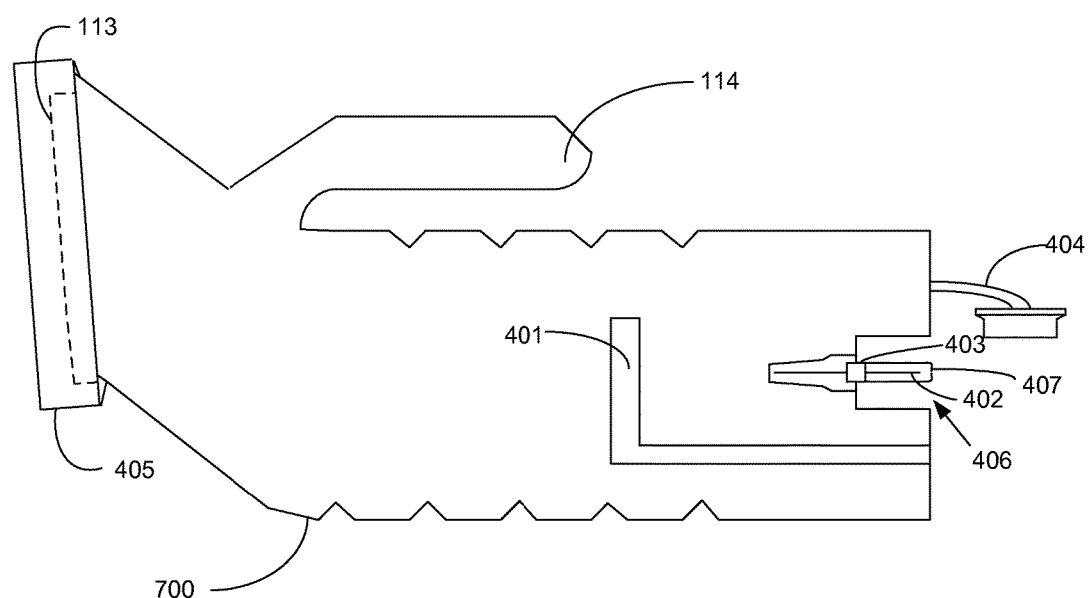
FIG. 7 shows a urinal similar to that of FIG. 4 but adapted for use by a female.

FIG. 7 shows a urinal 700, similar to that of FIG. 4, but adapted for use by a female.

In preferred embodiments, the connection of the analysis vial to the urinal automatically allows the flow of urine from the urinal to the analysis vial, and disconnection of the analysis vial automatically stops the flow from the urinal opening. While the embodiments described above use a needle mounted on the urinal to transfer urine from the urinal to the analysis vial, as described above, different mechanisms can be used that allow the urine to flow when the analysis vial is attached and that stop the flow when the analysis valve is no longer connected. In preferred embodiments, the connection mechanism prevents urine from leaking outside of the urinal and analysis vial during connection, transfer, and disconnection.

While in the embodiment described above uses a vacuum in the analysis vial to cause the urine to flow, other embodiments can use gravity to cause the urine to flow into the analysis vial. In some embodiments, a pressure differential between the urinal and the analysis valve can be achieved by raising the pressure in the urinal rather than having a vacuum in the analysis valve.

According to some embodiments of the invention, a urine collection apparatus comprises a storage container for holding urine; a first closeable opening in the storage container for allowing urine to enter and exit the storage container, the shape of the opening configured for contacting a bedridden patient to allow the patient to urinate into the storage container; a second opening for allowing fluid transfer from the interior of the storage container to the exterior of the storage container; and a seal for the second opening, the seal maintaining the urine within the storage container being sealed until an analysis vial is connected to the urine collection apparatus, the connection of the analysis vial opening the seal to allow urine to leave the storage container when the analysis vial is connected.

In some embodiments, the analysis vial is connected to the urine collection apparatus through a needle. In some embodiment, the urine collection apparatus further comprises a rubber sheath, the rubber sheath covering the portion of the needle exterior to the storage container, the rubber sheath being retractable.

In some embodiments, the analysis vial comprises the needle. In some embodiments, the urine collection apparatus comprises the needle. In some embodiments, the urine collection apparatus further comprises a needle holder in the wall of the storage container for maintaining the needle in a fixed orientation.

In some embodiments, the fixed orientation is perpendicular to the wall of the storage container. In some embodiments, the urine collection apparatus further comprises a barrier extending from the wall of the storage container, the barrier pooling urine to be in contact with the second opening. In some embodiments, the interior of the storage container is at a higher pressure than the interior of the analysis vial.

In some embodiments, the seal for the second opening comprises a stopper. In some embodiments, the urine collection apparatus further comprises a female adapter, the female adapter attaching to the first closeable opening in the storage container, the female adapter providing a boundary extending from the opening in order to facilitate fluid flow into the storage container.

According to some embodiments of the present invention, a urine collection apparatus comprises a storage container for holding urine; an opening in the storage container for allowing urine to enter and exit the storage container, the opening adapted for use by a bedridden patient; a needle for allowing fluid transfer from the interior of the storage container to the exterior of the storage container, a first portion of the needle being inside the storage container and a second portion of the needle being exterior to the storage container; and a barrier extending from the wall of the storage container, the barrier pooling urine to be in contact with the first portion of the needle.

In some embodiments, the urine collection apparatus further comprises a seal for sealing the needle, the seal maintaining urine within the apparatus. In some embodiments, an analysis vial is connected to urine collection apparatus through the needle, the connection between the analysis vial and the urine collection apparatus initiating fluid transfer from the urine collection apparatus to the analysis vial.

According to some embodiments of the present invention, a method of collecting and transferring urine using a urine collection apparatus comprises collecting urine in a urine collection apparatus, the urine collection apparatus comprising a first closeable opening configured for contacting a bedridden patient to allow the patient to urinate in the urine collection apparatus, a second opening for allowing fluid transfer from the interior of the storage container to the exterior of the storage container, and a seal for sealing the second opening, the seal maintaining the urine within the apparatus; connecting an analysis vial to the urine collection apparatus, the connection of the analysis vial opening the seal to allow urine to leave the storage container when the analysis vial is connected; filling the analysis vial with a desired amount of urine; and disconnecting the analysis vial from the urine collection apparatus once the desired amount of urine has entered the analysis vial, the disconnection of the analysis vial from the urine collection apparatus closing the seal to prevent urine from leaving the urine collection apparatus.

In some embodiments, the analysis vial is connected to the urine collection apparatus through a needle in the urine collection apparatus. In some embodiments, the analysis vial is connected to the urine collection apparatus through a needle in the analysis vial. In some embodiments, the needle is covered by a rubber sheath, the rubber sheath retracting to expose the needle when the analysis vial connects to the urine collection apparatus. In some embodiments, the method further comprises pooling urine near the second opening of the urine collection apparatus using a barrier in the urine collection apparatus before filling the analysis vial with a desired amount of urine.

Although the present invention and its advantages have been described in detail, it should be understood that various changes, substitutions and alterations can be made herein without departing from the spirit and scope of the invention as defined by the appended claims. The scope of the present application is not limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein, may be utilized according to the present invention. Accordingly, the appended claims are intended to include within their scope such processes, machines, manufacture, compositions of matter, means, methods, or steps.

I claim:

1. A urine collection apparatus, comprising:
a storage container for holding urine;
a closeable opening in the storage container for allowing urine to enter and exit the storage container, the perimeter of the opening configured for contacting a patient to allow the patient to urinate into the storage container;
a needle holder disposed in a wall of the storage container for maintaining a needle in a fixed orientation and for allowing fluid transfer from an interior of the storage container to an exterior of the storage container by way of the needle;
the needle disposed in the needle holder of the storage container, a first end of the needle extending beyond one side of the needle holder into the inside of the storage container and a second end of the needle extending beyond the other side of the needle holder to the exterior of the storage container;
a rubber sheath covering the second portion of the needle, the rubber sheath forming a seal maintaining the urine within the storage container until an analysis vial is connected to the second portion of the needle, the rubber sheath retracting to expose an opening in the needle when the analysis vial is connected to the needle, thereby allowing urine to flow from the storage container to the analysis vial; and
a barrier extending from an external wall of the storage container such that the barrier is spaced from the external wall, the barrier pooling urine to be in contact with the first portion the needle.

2. The urine collection apparatus of claim 1 in which the analysis vial is connected to the urine collection apparatus through the needle.

3. The urine collection apparatus of claim 1 in which the interior of the storage container is at a higher pressure than the interior of the analysis vial.

4. The urine collection apparatus of claim 1 in which the fixed orientation is perpendicular to the wall of the storage container.

5. The urine collection apparatus of claim 1 further comprising a female adapter, the female adapter attaching to the closeable opening in the storage container, the female adapter providing a boundary extending from the opening in order to facilitate fluid flow into the storage container.

6. The urine collection apparatus of claim 3 in which the needle is adapted for piercing an elastomeric stopper sealing the analysis vial so that urine can be drawn into the analysis vial by way of the higher pressure in the storage container.

* * * * *